United States Patent [19]
Rayburn

[11] Patent Number: 5,800,361
[45] Date of Patent: *Sep. 1, 1998

[54] NON-INVASIVE ESTIMATION OF ARTERIAL BLOOD GASES

[75] Inventor: Daniel B. Rayburn, Centerville, Va.

[73] Assignee: NTC Technology Inc., Wilmington, Del.

[*] Notice: The term of this patent shall not extend beyond the expiration date of Pat. No. 5,632,281.

[21] Appl. No.: 592,726

[22] Filed: Jan. 26, 1996

Related U.S. Application Data

[63] Continuation-in-part of Ser. No. 384,519, Feb. 6, 1995, Pat. No. 5,632,281.
[51] Int. Cl.$^6$ ........................................................ A61B 5/08
[52] U.S. Cl. .................... 600/532; 128/204; 600/529; 600/538; 600/543
[58] Field of Search ............................ 128/716, 719, 128/725, 726, 730, 204; 600/529, 532, 538, 539, 543

[56] References Cited

U.S. PATENT DOCUMENTS

| | | |
|---|---|---|
| 4,608,995 | 9/1986 | Linnarsson et al. . |
| 4,909,259 | 3/1990 | Tehrani . |
| 4,947,860 | 8/1990 | Fisher . |
| 4,986,268 | 1/1991 | Tehrani . |
| 5,339,818 | 8/1994 | Baker et al. . |
| 5,355,880 | 10/1994 | Thomas et al. . |
| 5,402,796 | 4/1995 | Packer et al. . |

OTHER PUBLICATIONS

Blanch, Lluis, et al., "Relationship Between Expired Capnogram and Respiratory System Resistance in Critically Ill Patients During Total Ventilatory Support", *Chest*, vol. 105; No. 1; ISSN: 0012-3692 (Database version of article), Jan. 1994.

Bongard, Fred, et al., Pulse Oximetry and Capnography in Intensive and Transitional Care Units; Summary from the Medical-Surgical Critical Care Conference, Harbor-UCLA Medical Center, California Medical Association, *The Western Journal of Medicine*, vol. 156; No. 1; ISSN: 0093-0415 (Database version of article), Jan. 1992.

Callaham, Michael, "Measuring Exhaled Carbon Dioxide in Cardiac Arrest; Emergency Medicine", California Medical Association, *The Western Journal of Medicine*, vol. 151; No. 1; ISSN: 0093-0415 (Database version of article), Jul. 1989.

Fletcher, Roger, The Single Breath Test for Carbon Dioxide, University of Lund, Lund, Sweden, 1980; pp. 1–113 (entire work).

Jordanoglou, J., et al, "Measurement of Effective Alveolar Carbon Dioxide Tension During Spontaneous Breathing in Normal Subjects and Patients With Chronic Airways Obstruction" *Thorax*, University of Athens, Medical School, Athens, Greece, Nov. 16, 1994.

Maltais, Francois, et al., "Respiratory Mechanics In Status Asthmaticus: Effects of Inhalational Anesthesia", *Chest*, vol. 106; No. 5; ISSN: 0012-3692 (Database version of article), Nov. 1994.

(List continued on next page.)

*Primary Examiner*—Jennifer Bahr
*Assistant Examiner*—Stephen Huang
*Attorney, Agent, or Firm*—Trask, Britt & Rossa

[57] ABSTRACT

A non-invasive system and procedure for deriving the blood gas content for a patient. The system measures the carbon dioxide concentration of the expiratory breath relative to volume. This data is then processed to derive arterial blood gas levels of carbon dioxide. If data sampling is in the time domain, the processing shifts the data from the time domain to the volume domain. The processing also iteratively assesses the significance of numerous variables. The resulting relationship provides a fast and accurate measure of blood gas content for both healthy and diseased lung patients.

19 Claims, 4 Drawing Sheets

OTHER PUBLICATIONS

Sanders, Mark H., et al. "Accuracy of End–Tidal and Transcutaneous $PCO_2$ Monitoring During Sleep", *Chest*, vol. 106; No. 2; ISSN: 0012–3692 (Database Version of Article); Aug. 1994.

Weil, Max Harry, et al., "End Tidal $PCO_2$ During Cardiopulmonary Resuscitation; Carbon Dioxide Tension", *The Journal of American Medical Association*, vol. 263; No. 6; ISSN: 0098–7484; (Database version of article), Feb. 9, 1990.

Zimmerman, Mark, et al, "Estimated vs. Actual Values for Dead Space/Tidal Volume Ratios During Incremental Exercise in Patients Evaluated for Dyspnea", *Chest*, vol. 106; No. 1; ISSN: 0012–3692 (Database version of article); Jul. 1994.

NON-INVASIVE ESTIMATION OF ARTERIAL BLOOD GASES

This application is a continuation-in-part of U.S. patent application Ser. No. 08/384,519, filed Feb. 6, 1995, now U.S. Pat. No. 5,632,281.

BACKGROUND OF THE INVENTION

1. Field of the Invention

The present invention relates to methods and apparatus for assessing the ventilatory status of a patient. More particularly, the present invention provides a system for implementing a non-invasive procedure for estimating the amount or concentration of dissolved carbon dioxide within the arterial portion of the vasculature. The arterial carbon dioxide content, expressed as a partial pressure, i.e., $pCO_2$ is an important measure of ventilatory status which ultimately reflects pulmonary health.

2. State of the Art

Physicians and other health care providers often use elevated arterial $pCO_2$ ($PaCO_2$) as an indicator of incipient respiratory failure. In this regard, the determination of $PaCO_2$, is useful in optimizing the settings on ventilators and detecting life-threatening blood gas changes in an anesthetized patient undergoing surgery. The traditional method for obtaining arterial blood gas values is to extract a sample of arterial blood and measure the partial pressure of carbon dioxide using a blood gas analyzer ($PaCO_2^{ABG}$). Arterial puncture has inherent limitations: 1) arterial puncture carries a degree of patient discomfort and risk, 2) handling of the blood is a potential health hazard to health care providers, 3) significant delays are often encountered before results are obtained and, 4) measurements can only be made intermittently.

Continuous invasive monitoring requires in-dwelling arterial lines which entail inherent problems. These include sepsis, slow response times, and signal decay. The nature of this monitoring systems excludes its use under routine care and is generally restricted to intensive care units within a hospital facility.

Figure 1:
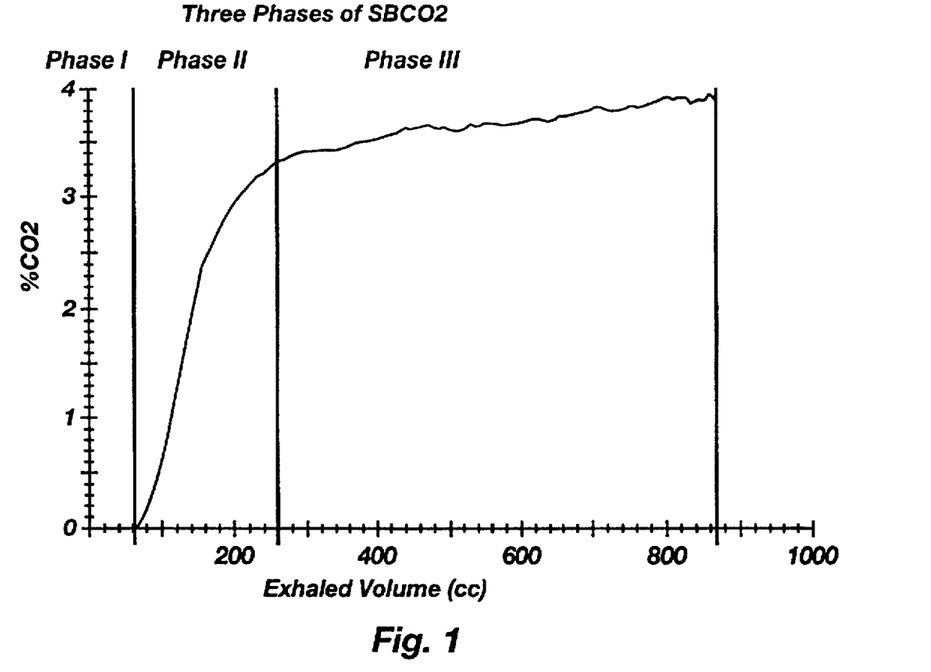
FIG. 1 graphically illustrates three phases of the $CO_2$/volume curve in a healthy person.
Figure 2:
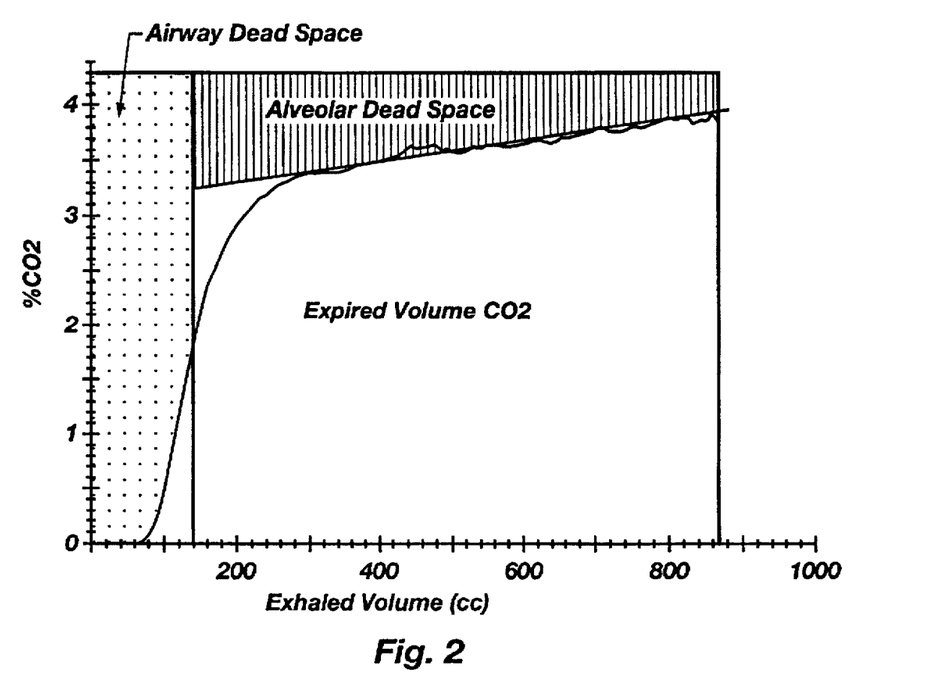
FIG. 2 represents the normal expiration of $CO_2$ plotted against the expired volume and the represented dead spaces.

There have been attempts to assess $PaCO_2$ levels indirectly, including a technique known as capnography. The approach utilized in capnography involves tracking patient exhalation and measuring expiratory gas $CO_2$ concentration against time during one or more respiratory cycles. The resulting relationship is plotted to create a graph depicting three distinct phases in breath $CO_2$ gas concentration during the patient exhale cycle. (See, FIG. 1). Typically, the three phases reflect the clearing of the conducting airways which do not normally participate in gas exchange (i.e., airway dead space) (phase I) followed by the exhalation of air from conducting airways dynamically mixed with lung gases from the active (alveoli) membrane surfaces within the lung that have undergone gas exchange with arterial blood (Phase II). The final phase (phase III) reflects the exhalation of unmixed gas from regions of the lung which are normally in active exchange with the alveoli tissue. Phase III thus closely resembles (in healthy patients) gas properties associated with arterial blood in contact with the lung for gas exchange ($CO_2$ release and $O_2$ absorption). In normal lungs, the graph line of Phase III is substantially level (slope=0) since ventilated and perfused alveolar regions are closely matched. In a diseased lung, the Phase III line may not appear level due to a mismatch in ventilation and perfusion of this lung region. See, Table I below:

TABLE I

| Phase I | Represents $CO_2$-free gas expired from the airway conduction structures where gas exchange does not occur, |
|---|---|
| Phase II | The S-shaped upswing in $CO_2$ concentration (expressed as a percent) represents the transition from airway to alveolar gas, and |
| Phase III | The alveolar plateau representing $CO_2$ rich gas from the alveoli. |

In the past, capnography has utilized the peak or end-tidal ($PetCO_2$) values as an estimate of $PaCO_2$. $PetCO_2$ is a measure of the mean alveolar partial pressure of carbon dioxide from all functional gas exchange units of the lung. $PetCO_2$ obtained from capnography is a measure of mean alveolar $pCO_2$, which value approximates $PaCO_2$ in normal lungs. Because $CO_2$ readily diffuses across the alveolar-capillary membrane, the $PetCO_2$ closely approximates the $PaCO_2$ with normal ventilation-perfusion. The difference between $PetCO_2$ and $PaCO_2$ is primarily a function of the proportion of the lung where gas exchange does not occur (Fletcher, R., Johnson, G., and Brew, J., The Concept of Deadspace with Special Reference to Single Breath Test for Carbon Dioxide. Br. J. Anaesth., 53, 77, 1981). In patients afflicted with a lung disease, there often exists a proportional increase in the region of the lungs where gas exchange does not occur. This increase in so-called "alveolar dead space" results in a significant difference between peak $CO_2$ ($PetCO_2$) obtained from capnography and elevated arterial $CO_2$ ($PaCO_2$).

Other techniques have been utilized for assessing patient blood gas levels with mixed results. Transcutaneous sensors measure tissue $pCO_2$ diffused through the heated skin but have practical and theoretical limitations. Oximetry is a widely used, non-invasive method for estimating the arterial oxygen carried on hemoglobin. For example, U.S. Pat. Nos. 4,759,369, 4,869,254 and 5,190,038 describe pulse oximeters which measure the percentage of hemoglobin which is oxygenated. However, neither of the aforementioned techniques measures the amount of dissolved oxygen present, nor the amount of oxygen carried when hemoglobin levels are reduced. Low hemoglobin levels are found when there is a significant blood loss or when there is insufficient red blood cell formation. Additionally, oximeter readings are specific to the point of attachment, which is typically the finger tip or ear lobe, and may not reflect the oxygen level of vital organs during conditions such as shock or hypothermia.

There remains a significant need in the art for an accurate, non-invasive, sensitive method for accurately determining the levels of arterial blood gases. As will be seen hereinafter, the instant invention sets forth a non-invasive system to overcome the problems of the prior art.

SUMMARY

The present invention provides a system to rapidly and accurately derive a patient's arterial carbon dioxide concentration and employs a non-invasive method for monitoring arterial partial pressure of carbon dioxide in a patient as an indicator of ventilatory status.

The present invention also comprises a system for detecting expiratory $CO_2$ concentration and volumetric rate data and accurately deriving actual arterial $pCO_2$ based thereon. The system affords non-invasive, substantially real time, determination of blood gas concentrations as derived from current expiratory data as correlated with processed data collected from past expiratory measurements.

The present invention converts expiratory data from a time domain to a volume domain or by accumulating data in the volume domain in the first instance. The arterial $CO_2$ partial pressures of a patient can then be ascertained by selectively analyzing the slope and intercept values associated with Phase II and Phase III expiratory data in the volume domain. If time domain data is converted to the volume domain, the conversion may be said to "normalize" the data by placing it in the volume domain, wherein time-dependent respiratory differences between patients are eliminated and a standardized gas concentration-to-incremental breath volume relationship is achieved.

The present invention also provides for the accurate determination of arterial $CO_2$ partial pressures by measuring expiratory gas data and statistically filtering this data to ascertain readings having the highest correlation to actual pulmonary performance with a statistically significant level of confidence.

The above and other advantages of the present invention are realized in a specifically delineated gas analysis and data processing system operated in accordance with select data qualifying and enhancing procedures. In particular, the inventive system provides for the collection of concise expiratory data from a patient undergoing treatment. This data includes details on $CO_2$ gas partial pressure, concentration, and total gas volume sampled during breath exhaust cycle. Multiple readings are made to enhance accuracy. The expiratory data is converting to a volume domain from the time domain. The expiratory data is then charted to establish the three aforementioned distinct phases within the expiratory cycle. The associated linear details of these three phases are extracted and used to project current arterial $CO_2$ partial pressure, $PaCO_2$. This value is then utilized to quantify pulmonary performance and/or determine the existence of lung failure or distress.

In accordance with the varying aspects of the present invention, the system includes a sophisticated artificial intelligence engine that iteratively analyzes many separate and distinct measurements and the calculated values associated with the expiratory data. Based on these permutations, the engine quantifies those measured and derived values having the highest correlation to the actual arterial $CO_2$ partial pressures, resulting in a fixed relationship including specifically weighted variables for projecting arterial $CO_2$ partial pressures. This relationship, expressed as a vector, is implemented according to system parameters in actual patient monitoring during surgical procedures and other periods of time associated with potential pulmonary failure.

BRIEF DESCRIPTION OF THE DRAWINGS

The foregoing features of the present invention are more fully and readily understood from the following detailed description of a specific illustrative embodiment thereof, presented hereinbelow in conjunction with the accompanying drawings of which.

DETAILED DESCRIPTION OF THE PREFERRED EMBODIMENT

In overview, the present invention comprises a non-invasive system and procedure for deriving the gas content of arterial blood through analysis of the expiratory gas concentrations and volumes. The expiratory gas concentrations and volumes may be collected in a time domain, typically using a capnometer and pneumotachometer. Alternatively, the data may be collected directly in the volume domain with a time delay or phase-shift correction between the pneumotachometer and capnometer data. The raw data for both $pCO_2$ and volume are digitized at a frequency high enough to avoid aliasing. In adults with normal ventilatory frequencies, the data is typically collected at 100 Hz, producing a data point every 0.01 seconds. If taken in the time domain, the measurements are converted from the time domain (typically 1 point per 0.01 seconds) to a volume domain (typically 1 point per 1 ml of expired volume) utilizing a polynomial fit.

In the volume domain, the slope of the Phase II curve segment is calculated. The initial point of Phase II is where the curve transcends a threshold value (typically 0.5% for adults). The final point of Phase II is defined, in this application, as the point at which the curve deviates from linearity by a specified amount (typically 5% for adults). The threshold and deviation values are based on lung size and respiration rate. The slope of the Phase III segment is calculated, in an analogous manner, by calculating from the last data point of expiration toward Phase II until the curve deviates from linearity by a fixed amount (typically 5% for adults). The slopes of the Phase II and Phase III curve segments are used as initial input variables, which variables are combined into a vector with other parameters to produce an estimate of content of the gas in the arterial blood, i.e., the partial pressure of $CO_2$, or $PaCO_2$.

The following abbreviations and definitions are salient to invention description:

| ABBREVIATIONS AND DEFINITIONS | |
|---|---|
| $CO_2$ | Carbon dioxide |
| $pCO_2$ | Partial pressure of carbon dioxide |
| $PetCO_2$ | End tidal $CO_2$ |
| $PECO_2$ | Expiratory $CO_2$ |
| $PaCO_2$ | Arterial partial pressure of $CO_2$ |
| $PaCO_2^{ABG}$ | Arterial partial pressure of $CO_2$ measured by an arterial blood gas analyzer |
| % $CO_2$ | Carbon dioxide value expressed as a percentage of the total gas content |
| COPD | Chronic obstruction pulmonary disease |
| ml | Milliliters |
| fds | Fowler dead space (Airway dead space) |
| I2 | Intercept of Phase II on $CO_2$ axis |
| I3 | Intercept of Phase III on $CO_2$ axis |
| m2 | Slope of Phase II |
| m3 | Slope of Phase III |
| ph2i | Phase II deviation index |
| ph3i | Phase III deviation index |
| Tb | Phase transition bend |
| Tbi | Phase transition bend index |
| TV | Tidal volume of air exhaled |
| ang | Angle between Phases II and III |

Figure 5:
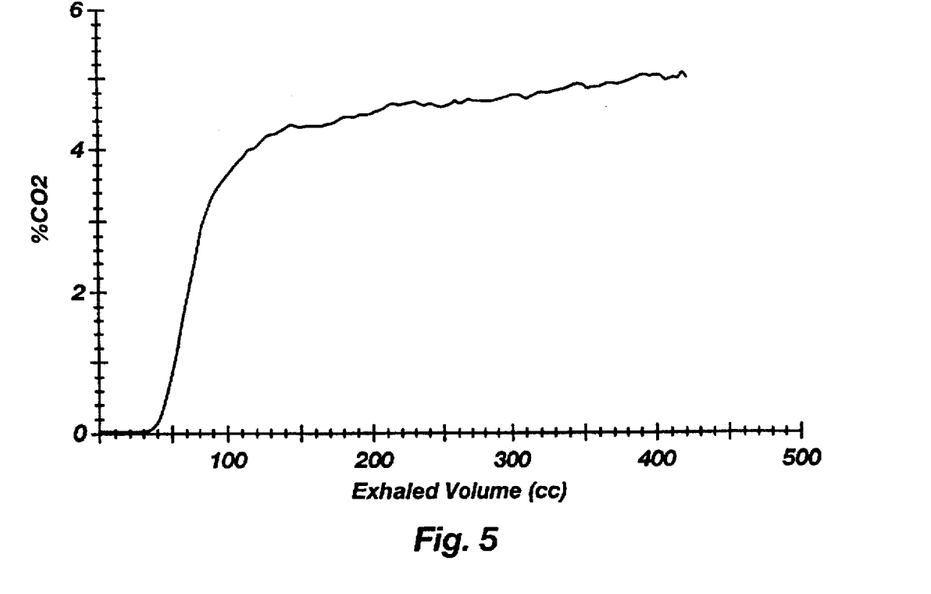
FIG. 5 is a capnograph for a healthy individual.

As noted above, expired $CO_2$ pattern obtained from capnography may be graphically depicted as a three-phase curve. In a normal person (FIG. 5), the $CO_2$ curve forms a plateau at the start of Phase III and reaches a value ($PetCO_2$) approximately equal to the $PaCO_2$ at the end of Phase III. In a patient with increased volume of the lung where gas exchange does not occur (physiologic or alveolar dead space, FIG. 6), as typically occurs in COPD, the curve does not plateau and the final $PetCO_2$ values are a less reliable indication of the actual $PaCO_2$. The instant invention determines an estimated value which closely approximates the actual $PaCO_2$ under these and other conditions.

Figure 3:
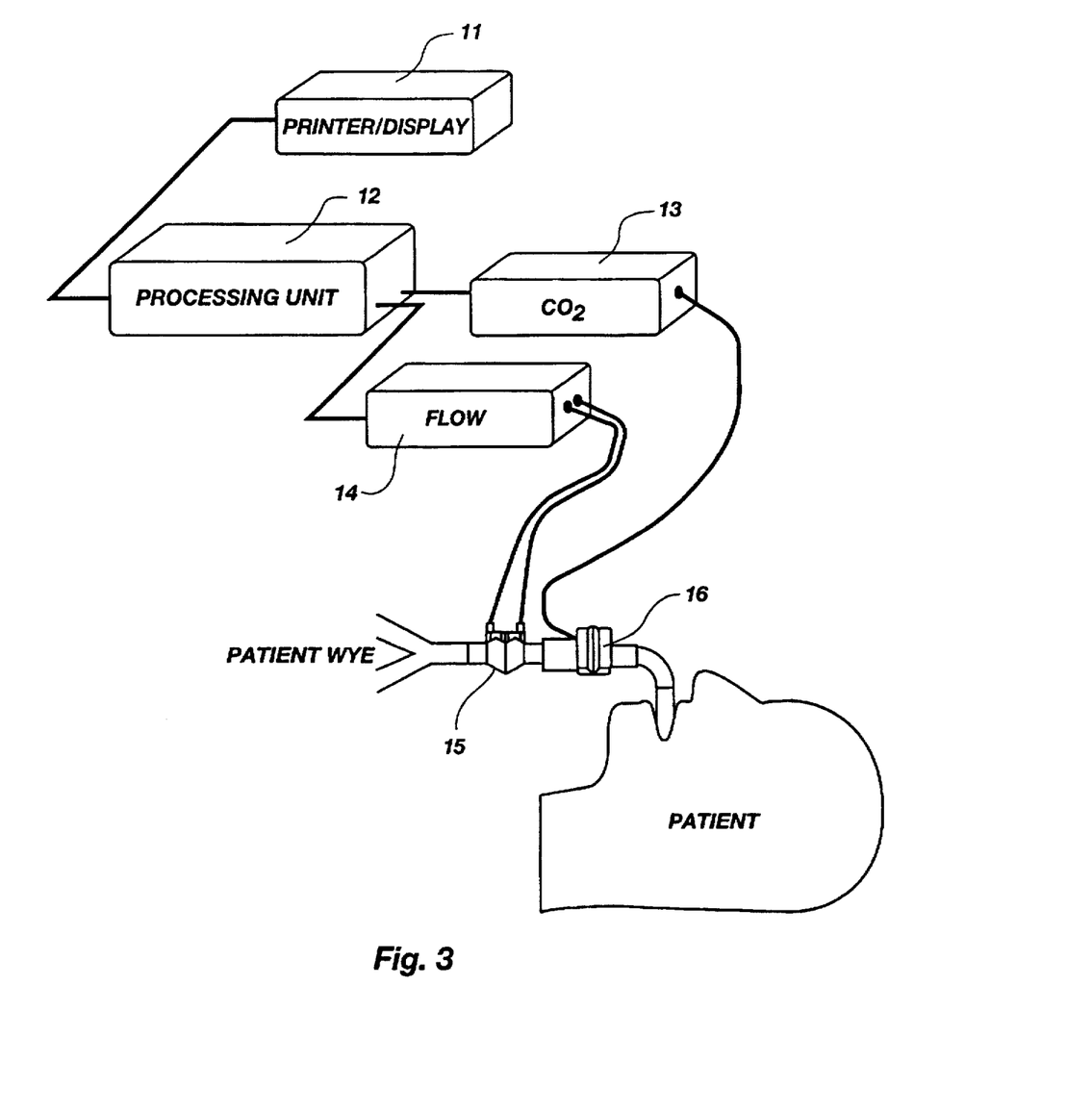
FIG. 3 is a schematic illustration of a system in accordance with a preferred embodiment of the present invention.

The inventive system is illustrated in FIG. 3 and comprises a differential pressure flowmeter or pneumotachometer (item 15), a flow signal unit (item 14), a gas sensor (item 16), a $CO_2$ signal unit (item 13), a processor (item 12) and a data display (item 11). This system can be used with or without mechanical ventilation of the patient.

Many devices for measuring the volume of a person's expiratory breath already possess the capability to integrate a measured flow and can be used in this invention. Typically, flow-measuring devices use one of the following methods to determine flow:

1. measurement of pressure drop or differential pressure across a fixed resistance (differential pressure flowmeter or pneumotachometer),
2. measurement of the temperature change of a heated wire cooled by the airflow (hot wire anemometer),
3. measurement of frequency shift of an ultrasonic beam passed through the airstream (ultrasonic Doppler),
4. counting the number of vortices shed as air flown past a strut (vortex shedding), or
5. measurement of transmission time of a sound or heat impulse created upstream to a downstream sensor (time of flight device).

Alternatively, volume may be measured directly by counting revolutions of a vane placed in the flow path (spinning vane). A discussion of the aforementioned devices and associated technology can be found in Sullivan, et al., *Pneumotachographs: Theory and Clinical Application*, Respiratory Care, Vol. 29-7, pages 736–749 (1984), which is incorporated by reference herein. Examples of known differential pressure flowmeters include those described in U.S. Pat. Nos. 4,047,521, 4,403,514, 5,038,773, 5,088,332, 5,347,843 and 5,379,650, the teachings of which are incorporated by reference herein.

The exemplary device for respiratory flow measurement is the differential pressure flowmeter or "pneumotachometer" (FIG. 3, item 15), which provides a pressure differential indicative of respiratory flow, the differential being converted via transducers in flow signal unit (item 14) to electrical signals representative of the relationship between respiratory flow and pressure differential. The flowmeter (item 15) is manufactured and sold by Novametrix Medical Systems, Inc., Wallingford, Conn. However, any of the aforementioned types of flow measurement devices may be utilized in the inventive system.

Sensors capable of measuring carbon dioxide content in a person's expiratory breath are well known. The currently preferred device for measuring carbon dioxide content is a gas analyzer of the type employing non-dispersive infrared radiation which presents data representing the % $CO_2$ (or $pCO_2$) of a sample of exhaled breath. Examples of known infrared gas analyzers include those described in U.S. Pat. Nos. 4,859,858, 4,859,859, 4,914,720, 4,958,075, 5,146,092, 5,153,436, 5,206,511 and 5,251,121, the teachings of which patents are incorporated by reference herein. Other technologies used to measure the concentration of carbon dioxide such as Raman spectroscopy and mass spectroscopy can also be used in the present invention.

The exemplary gas sensor (FIG. 3, item 16) capable of measuring carbon dioxide content in a patient's exhaled breath is available from Novametrix Medical Systems, Inc., Wallingford, Conn., under the trade name CAPNOSTA™. Other methods of measuring carbon dioxide content both at the airway (mainstream) or by removing a sample (sidestream) may be used in the present invention.

Gas analyzers as described above employ non-dispersive infrared radiation to measure the concentration of a selected gas in a mixture of gases. The infrared radiation can be emitted from a thick film source and focused by a mirror to pass through the mixture of gases being analyzed. After passing through the gas mixture, the infrared beam is passed through a filter which reflects all of the radiation except for those in the narrow bands centered on a wavelength which is absorbed by the gas of concern (such as $CO_2$) in the mixture being analyzed (such as the air flow from a person's expired breath). This narrow band of radiation, which typically extends approximately 190 angstroms to each side of the wavelength on which the radiation is centered, is allowed to reach a detector which is capable of producing an electrical output signal inversely proportional to the magnitude of the infrared radiation impinging upon it, as the radiation in that band is attenuated to an extent which is proportional to the concentration of the designated gas in the mixture of gases being analyzed. The strength of the signal generated by the detector is consequently inversely proportional to the concentration of the designated gas and can be inverted to provide a signal indicative of that concentration. The processor can be either a personal computer with a suitable digital interface for receiving the digital signals from the $CO_2$ signal unit (FIG. 3, item 13) and flow signal unit (FIG. 3, item 14), or any specially designed processor capable of calculating the vectors as disclosed further herein.

As discussed above, capnography systems in the prior art have attempted to estimate the $PaCO_2$ by using the peak or end-tidal value for a single breath ($PetCO_2$). Such systems are effective at tracking gas changes in normal lungs but have been shown to be unreliable in diseased lungs such an COPD or when a significant pulmonary shunt exists. The inadequacy of $PetCO_2$ to measured $PaCO_2$ is in part attributed to regions within the lung with high ventilation to perfusion ratios. Exhaled gases from regions where gas exchange does not occur due to inadequate perfusion reduce the obtained $PetCO_2$. For example, in the diseased lung, the increased slope of Phase III due to impaired gas exchange makes the $PetCO_2$ valve a less reliable indicator of $PaCO_2$.

Figure 6:
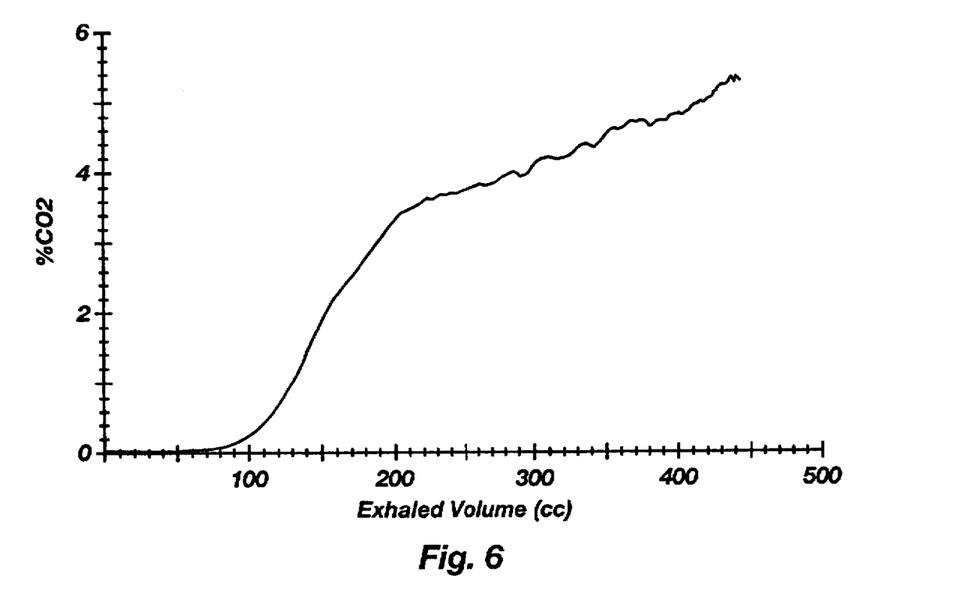
FIG. 6 is a capnograph of a person suffering from lung distress.

In the instant invention, the digitized expired $CO_2$ and flow data, if taken in the time domain, is converted to the volume domain to account for variations between different people and thereby improve accuracy. Alternatively, flow signal unit 14 may be employed to integrate a flow rate signal on a continuing basis into volume, $CO_2$ readings then being taken at predetermined volumetric intervals, the phase shift between the two sensors (including signal processing time) being corrected for as data is taken or subsequently processed. Alternatively, all data may be taken in the time domain and converted to the volume domain after the fact by processing unit (FIG. 3, item 12). Finally, as previously noted, flow volume may be measured directly, as by a spinning vane device. $CO_2$ concentrations versus respiratory flow or volume may be depicted as a curve including a series of units, each defined by a pair of points. In the time domain, the progression from unit to unit is based on fractions of a second, regardless of the quantity of air expelled during that time period. The effective rate of sampling depends on the patient's rate of respiration. In the volume domain, however, each unit to unit movement is based on a unit of volume of air expelled, regardless of the expiratory time. By employing a volume domain or by transferring the data from a time domain to a volume domain a more physiologic relationship is expressed. Toward the end of the breath, relative percentage increments in expiratory time and volume vary greatly in magnitude, particularly when comparing healthy individuals to patients with impaired respiratory function. By using the volume domain, the latter portion of the breath receives a weighting more indicative of its physiologic importance regardless of the health of the patient. For example, in a mechanically ventilated, chemically paralyzed, patient with COPD experiencing bronchospasm, the exhalation period is prolonged due to the narrowing of the airways (FIG. 6). With pharmaceutical intervention, expiratory resistance can be reduced, thereby reducing time required to complete exhalation. The exhalation time greatly varies between the non-medicated and medicated patient, yet the exhaled $CO_2$ to total gas volume exhaled ratio is relatively constant. Plotted in the volume domain, the capnograph of non-medicated and medicated patients would be the same. Conversely, in the prior art systems (time domain), measurements taken before and after medication would vary greatly.

As shown in FIG. 3, as a person exhales, the $CO_2$ sensor (item 16) measures the $pCO_2$ in the person's expiratory breath. Virtually simultaneously, the pneumotachometer (item 15) measures the flow of the person's expiratory breath using differential pressures across a fixed resistance as previously referenced. The differential pressure values from the pneumotachometer (item 15) are converted to electrical signals and digitized in flow signal unit (item 14) and the analog signals from $CO_2$ sensor (item 16) are digitized in $CO_2$ signal unit (item 13). The digital signals are processed, as further disclosed herein, in the processor (item 12) and displayed via printer, VDT, LED or other display devices as known in the art (item 11). The estimated $PaCO_2$ value is displayed after several breaths. The actual lag time is dependent on the consistency of the data with a minimum of six breaths initially and every third breath thereafter. This data flow is illustrated, as part of the complete conversion routine, in FIG. 4. As stated heretofore, the $CO_2$ sensor (item 16) and associated signal unit (item 13) measures the $CO_2$ content of the patient's breath. The output from the flow sensor (item 15) is representative of the flow of the expiratory breath. The pneumotachometer (item 15) outputs are converted via transducers in flow signal unit (item 14) to electrical signals which are digitized as time dependent signals representing the flow rate of the patient's breath, and subsequently integrated into volume. These signals are sent to the processor (item 12).

Figure 4:
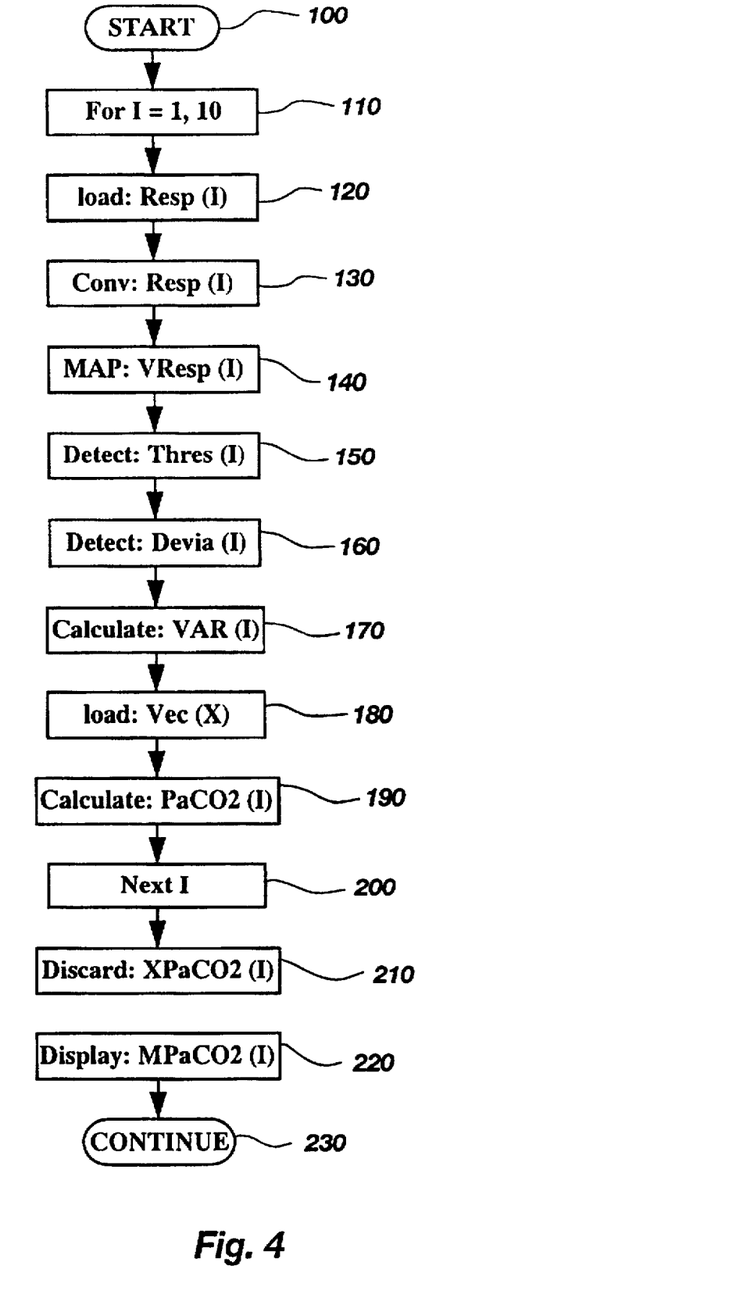
FIG. 4 is a flow chart of a preferred method of the present invention.

As shown in the flow chart in FIG. 4, the flow data and $CO_2$ data are isolated breath-by-breath and converted to the volume domain in order to express a more physiologic relationship. The volume domain progression from unit to unit is based on a unit of volume expired without regard to time. As a preliminary programming step, a variety of variables are computed which depict features of Phase II, the transition period, and Phase III. The computed variables are selected to include all features and idiosyncrasies of the capnograph. The derived variables are of two types: 1) those with established physiologic importance, and 2) those which mathematically represent features of the capnograph whose physiologic significance is less clear. These derived variables have utility in normalization of the data to allow for diverse lung sizes and respiratory patterns. Artificial intelligence is then used to evaluate each variable and assign a mathematical weight. In particular, a neural network is employed to insure the variables are evaluated without imposing an initial bias. These variables are computed as described hereafter.

Suitable software systems are readily available in the marketplace, and are exemplified by the neural network presently offered by NeuralWare, Inc. located at Penn Center West, Building IV, Suite 227, Pittsburgh, Pa. 15276.

COMPUTATION OF INTERMEDIATE VARIABLES

A threshold level of $CO_2$ is detected by finding the point were the curve transcends from a value below 0.5% to a value above 0.5%. In the instant invention, this point is used as the initial point of Phase II. From the threshold point, subsequent $CO_2$ data points are adjoined and tested for linearity to the data point where the signal deviates from a linear path. The amount of allowed deviation is typically 5% in adults. The point where the deviation occurs marks the termination of Phase II and the slope of the Phase II segment is derived. As described further herein, the Phase II slope is used later. The slope of Phase III is determined in an analogous manner by starting at the last data point of expiration (Pet $CO_2$) and regressing toward the termination point of Phase II. Once the Phase II and III slopes are computed, the remaining input variables are derived as the following:

TABLE II

| | |
|---|---|
| Fds | The Fowler dead space volume is determined by examining the volume that gives equal area between the start of the Phase II data and the start of the Phase III data. This computation is done by fractional difference. (Fowler W. S. Lung Function Studies II. The Respiratory Dead Space. Am. J. Physiol. 154: 405, 1948 - the teachings of which are hereby incorporated by reference). |
| i2 | The $CO_2$ axis intercept of Phase II. The effective Phase II slope (m0) is used at the Fds volume. The equation is: i2 = modelCO$_2$ (Fds) – m0 * Fds where modelCO$_2$ (Fds) is the model evaluated at Fds. |
| m3 | The slope of Phase III. |
| i3 | The $CO_2$ axis intercept of Phase III. The Phase III slope is used at the end tidal volume. The equation is: i2 = modelCO$_2$ (PetCO$_2$) – m3 * PetCO$_2$ where modelCO$_2$ (PetCO$_2$) is the model evaluated at PetCO$_2$. |
| ang | The angle in degrees between the Phase II and Phase III. The effective slope of Phase II (m0) is used. The angle between the lines is: (tan(m3) – tan(m0) + π) * (180/π). |
| PetCO$_2$ | The end tidal value of pCO$_2$. The last element in the CO$_2$(vol) data array is used for PetCo$_2$. |
| TV | The total volume of air exhaled expressed in ml. |
| ph2i | The Phase II deviation index. This is smallest volume at which the Phase II line deviates from the smoothed CO$_2$ data. The comparison is done by fractional difference. |
| ph3i | The Phase III deviation index. This is the smallest volume at which the Phase III line deviates from the smoothed CO$_2$ data by the phase transition width (Tw). The negative of the second derivative of the model curve exhibits a peak in the region between Phase II and Phase III. The width of this peak is Tw and is determined as the full width at half the maximum of the peak. All second derivative curves have peaks that fall below half the maximum of increasing volume. However, the peaks in some derivative curves do not fall to ½ the maximum for decreasing volume. Thus, Tw is found from the right side half-width of the peak at half-maximum and multiplying by 2 to construct the full-width. |
| Tb | The phase transition bend. This value is the maximum of the negative of the second derivative of the model curve. It reflects the measure of the sharpness of the transition. |
| Tbi | The phase transition bend index. This value is the index (volume) at which the phase transition bend (Tb) occurs. |
| Mod-Ang | A modified version of the angle in degrees between the Phase II and Phase III lines. The modification scales the actual angle to enhance differences in the model fit curves. The scaling is heuristic. The modified angle is computed as: (tan(400 * m3) – tan(400 * m0) + π)(180/π). |

The product of these intermediate variables and their assigned mathematical weights are used in arguments in a hyperbolic scaling function to compute the final $PaCO_2$. The mathematical weights for each variable were initially defined from a set of 100 derived variables used as inputs to a fully connected, back-propagation, neural network and the actual arterial carbon dioxide used as the desired output. Once trained for 75,000 iterations, the resultant weights were extracted and used for subsequent derivations where the actual $PaCO_2$ was to be determined.

System operation based on the stored vector arguments are shown in the flow chart in FIG. 4. As described herein, the system inputs the flow data and $CO_2$ data as isolated breath-by-breath and converted to the volume domain in order to express a more physiologic relationship. The volume domain progression from unit to unit is based on a unit of volume expired without regard to time. Referring to FIG. 4, logic begins at start block 100, and begins a processing loop defined by block 110, defining a sequence of 10 iterations (exemplary). At block 120, the digitized respiratory data is loaded as variable RESP(I), converted to the volume domain at block 130, and then mapped, setting forth the three aforementioned phases of the capnograph, block 140, VRESP(I).

At block 150, Phase II threshold is detected, THRESH(I), followed by block 160 wherein the detection of the Phase II deviation to Phase III, DEVIA(I) is effected. Based thereon, the variables for the capnograph are determined, VAR(I), at block 170. The stored arguments based on the assessed weighting for the vector are recalled at block 180, and the final vector generated, VEC(I). Based thereon, the $PaCO_2$ is derived and stored for the Ith iteration, block 190. At block 200, this process is repeated for the next sequence of respiratory data from the patient, for 10 iterations or breath cycles (exemplary).

Starting at block 210, the data is refined by discarding four of the ten readings (two high and two low), XPaCO₂(I), and the resulting six iteratives are statistically assessed and accepted if meeting a minimum confidential level (95 or 99%), by way of example. If accepted, the mean value of the remaining iterations is displayed, MPaCO₂(I), block 220. The process continues giving pseudo real time data, as noted at block 230.

The results of system operation is depicted for the following patients:

TABLE III

| Derived $PaCO_2$ Patient No. | $PaCO_2{}^{ABG}$ | $PaCO_2$ mean | std | err |
|---|---|---|---|---|
| 1. | 33.00 | 34.30 | 2.40 | 1.30 |
| 2. | 33.00 | 31.33 | 1.84 | 1.67 |
| 3. | 33.00 | 32.20 | 2.33 | 0.80 |
| 4. | 33.50 | 32.00 | 1.77 | 1.50 |
| 5. | 38.30 | 39.67 | 1.36 | 1.39 |
| 6. | 40.00 | 38.37 | 0.86 | 1.63 |
| 7. | 40.00 | 41.38 | 0.62 | 1.38 |
| 8. | 42.00 | 42.63 | 0.15 | 0.63 |
| 9. | 42.00 | 44.01 | 1.60 | 2.01 |
| 10. | 44.00 | 45.47 | 0.18 | 1.47 |
| 11. | 45.00 | 45.66 | 2.35 | 0.66 |
| 12. | 46.00 | 46.40 | 1.31 | 0.40 |
| 13. | 47.00 | 47.42 | 0.96 | 0.42 |
| 14. | 49.00 | 51.03 | 0.12 | 2.03 |
| 15. | 50.50 | 50.73 | 0.50 | 0.23 |
| 16. | 51.00 | 49.77 | 0.31 | 1.23 |
| 17. | 51.00 | 52.07 | 1.29 | 1.07 |
| 18. | 51.00 | 52.22 | 0.69 | 1.22 |
| 19. | 53.00 | 53.20 | 0.72 | 0.20 |
| 20. | 57.00 | 56.60 | 1.22 | 1.00 |
| 21. | 63.00 | 63.34 | 0.23 | 0.34 |
| 22. | 65.00 | 62.20 | 0.77 | 2.80 |
| 23. | 67.00 | 64.98 | 0.62 | 2.02 |

The exemplary data was computed for each breath contained in a 2–5 minute collection period. The calculated $PaCO_2$ values and standard deviations included in Table III were determined by analysis of the median six (6) values of ten (10) consecutive breaths. The standard deviations for the six (6) median values for each patient were computed for assurance of reproducibility of the data. The computed values were then compared to the $PaCO_2{}^{ABG}$ values obtained simultaneously from an arterial blood gas sample. Using this method the accuracy for determination of $PaCO_2$ by the method of the instant invention is typically about ±2 mmHg. However, rather than outputting a single $PeCO_2$ value, the actual data range for a 95 or 99% confidence levels may be graphically displayed, as on the data display (FIG. 3, item 11).

Since other modifications and changes varied to fit particular operating requirements and environments will be apparent to those skilled in the art, the invention is not considered limited to the example chosen for the purposes of disclosure, and covers all changes and modifications which do not constitute departures from the true spirit and scope of this invention.

What is claimed is:

1. A non-invasive arterial gas partial pressure determination system, comprising:

expiratory gas sampling means for taking one or more samples of expiratory gases from a patient;

means for assessing said gas partial pressure with respect to expiratory volume for said sampled gas;

means for evaluating said sampled gas in terms of said assessed gas partial pressure and expiratory volume iteratively during an exhale cycle to develop a multi-variable relationship; and gas sampling data processing means for receiving data input representative of said multi-variable relationship and selectively processing said data input to determine at least one arterial gas partial pressure value for that patient.

2. The system of claim 1, wherein said multi-variable relationship is developed in a time domain, further comprising means for converting said multi-variable relationship from the time domain to a volume domain.

3. The system of claim 1, and further comprising memory means for storing a matrix of linear arguments recallable to form a vector for use by said data processing means in conjunction with said multi-variable relationship to determine a partial pressure for arterial $CO_2$.

4. A computer controlled data collection and processing method for monitoring arterial gas values for at least one gas, comprising:

sampling a patient's exhaled breath to determine a partial pressure of said at least one gas in said exhaled breath as a function of incremental breath volume during an exhale cycle;

segregating data from said functional determination into three distinct phases representative of gas concentration of said at least one gas during said exhale cycle;

extracting functional variables from at least two of said three distinct phases in terms of slope and intercept values;

recalling from memory a matrix of weighting parameters associated with said extracted functional variables;

creating a vector based on said extracted functional variables modified by said recalled weighting parameters; and determining an arterial gas value for said at least one gas based on said vector.

5. The method of claim 4, and further comprising calculating said matrix of weighting parameters by an artificial intelligence regimen assigning weight to individual variables based on adduced significance.

6. The method of claim 5, and further comprising sampling said exhaled breath at a frequency approximately between 10 and 1000 Hz.

7. The method of claim 6, and further comprising eliminating extreme calculated arterial gas values, statistically qualifying an average of multiple calculated preliminary arterial gas values, and determining the arterial gas value for said at least one gas.

8. The method of claim 7, and sampling said patient's exhaled breath at intervals corresponding to requirements of the patient.

9. A system for deriving blood gas concentration for a patient for at least one gas, comprising:

a) data acquisition means for measuring exhaled breath from said patient and determining concentration of at least one gas fraction thereof at volumetric increments of said exhaled breath; and b) data processing means for receiving data representative of said at least one determined concentration and extracting select parameters therefrom to form a relationship, and implementing said relationship to derive said blood gas concentration for said at least one gas.

10. The system of claim 9, and further comprising means for expressing the derived blood gas concentration as a partial pressure.

11. The system of claim 10 wherein said at least one gas is $CO_2$.

12. The system of claim 9 wherein said data processing means further includes a memory means for storing a matrix of weighting values to be applied to said relationship.

13. The system of claim 12 wherein said weighting values are calculated by iterative assessment of predictive gas concentrations compared to actual gas concentrations for said at least one gas.

14. A non-invasive method of determining blood gas content based on volume domain, comprising:

a) taking time domain measurements of a plurality of a patient's expiratory breath during at least one respiratory cycle using a pneumotachometer, and a gas sensor for sensing the concentration of said blood gas in said breath, said measurements being at a frequency approximately between 10 and 1000 Hz;

b) converting said time domain measurements to the volume domain;

c) mapping said volume domain data to form a curve;

d) determining a threshold point having a value for said concentration of said blood gas in said breath, whereat said curve transcends from a value below said threshold point value to a value above said threshold point value;

e) calculating a first phase slope for said curve wherein said threshold point is an initial phase point, plotting subsequent points until said points deviate from a linear path, said deviation indicating the termination of said first phase;

f) calculating a second phase slope for said curve by taking a last data point of expiration during said at least one respiratory cycle and regressing toward the termination point of said first phase;

g) extracting first phase and second phase slope values to create an expiratory relationship;

h) combining said expiratory relationship with stored arguments into at least one vector;

i) using said at least one vector to produce an estimate of the concentration of said blood gas in said blood; and j) visually displaying said gas content in said blood.

15. The method of claim 14 wherein said gas is $CO_2$.

16. The method of claim 15 wherein said threshold paint value is about 0.5% concentration of said blood gas.

17. The method of claim 15, and further determining a partial pressure of $CO_2$.

18. A non-invasive method of determining a dissolved gas content of an arterial portion of a patient's pulmonary vasculature expressed as a partial pressure comprising:

a) taking time domain measurements of a plurality of said patient's expiratory breaths using a pneumotachometer and gas sensor, at a frequency of about 100 Hz;

b) converting said time domain measurements to a volume domain;

c) mapping a curvature relationship of gas partial pressure versus gas volume;

d) determining a threshold point, said threshold point being the point where said curvature relationship transcends from a value below 0.5% of said gas partial pressure to a value above 0.5%;

e) calculating a first phase slope wherein said threshold point is an initial point and including plotting subsequent points until said points deviate from a linear path, said deviation indicating termination of said first phase;

f) calculating a second phase slope by taking a last data point of expiration and regressing toward the termination point of said first phase;

g) using the first and second phase slopes to quantify an expiratory gas relationship;

h) combining said relationship with stored arguments into at least one vector;

i) using said at least one vector to estimate partial pressure of said dissolved gas; and j) visually displaying said partial pressure of said dissolved gas.

19. The method of claim 18 wherein said dissolved gas is $CO_2$.

* * * * *

UNITED STATES PATENT AND TRADEMARK OFFICE
CERTIFICATE OF CORRECTION

PATENT NO : 5,800,361
DATED : September 1, 1998
INVENTOR(S) : Rayburn

It is certified that error appears in the above-identified patent and that said Letters Patent is hereby corrected as shown below:

In column 1, line 17, insert a comma after "$pCO_2$";
In column 1, line 24, delete the comma after "$PaCO_2$";
In column 1, line 39, change "systems" to --system--;
In column 1, line 50, change "patient" to --patient's--;
In column 1, line 53, change "phase" to --Phase--;
In column 1, line 57, change "phase" to --Phase--;
In column 2, line 64, delete the comma after "time";
In column 3, line 2, change "by accumulating" to --accumulates--;
In column 3, line 26, after "during" insert --a--;
In column 3, line 28, change "converting" to --converted--;
In column 4, line 35, delete the period after "$CO_2$";
In column 4, line 56, in the table titled ABBREVIATIONS AND DEFINITIONS, delete "Th" and insert --Tb--;
In column 4, line 61, after "above," insert --the--;
In column 5, line 25, change "flown" to --flows--;
In column 6, line 1, delete "CAPNOSTA™" and insert --CAPNOSTAT™--;
In column 6, line 36, change "an" to --in--;
In column 6, line 44, change "valve" to --value--;

UNITED STATES PATENT AND TRADEMARK OFFICE
CERTIFICATE OF CORRECTION

PATENT NO : 5,800,361
DATED : September 1, 1998
INVENTOR(S) : Rayburn

It is certified that error appears in the above-identified patent and that said Letters Patent is hereby corrected as shown below:

In column 6, line 55, after "by" insert --a--;
In column 7, line 1, insert a comma after "domain" (second occurrence);
In column 7, line 9, delete the comma after "paralyzed";
In column 7, lines 40-41, change "flow sensor" to --pneumotachometer--;
In column 7, line 54, after "variables" change "are" to --is--;
In column 8, line 8, change "were" to --where--;
In column 8, line 19, change "(Pet $CO_2$)" to --(Pet$CO_2$)--;
In column 8, line 39, after "between" delete "the";
In column 8, line 43, change "Pet$Co_2$" to --Pet$CO_2$--;
In column 8, line 44, after "is" insert --the--;
In column 8, line 56, Table II, delete "Th" and insert --Tb--;
In column 8, line 67, change "are" to --is--;
In column 9, line 10, change "are" to --is--;
In column 9, line 25, insert a comma after "DEVIA(I)";
In column 10, line 18, insert a comma after "method"; and
In column 10, line 21, after "for" delete "a";
In column 11, line 49, change "content" to --concentration--;
In column 11, line 50, after "taking" insert --a plurality of--;
In column 11, line 50, after "measurements" delete "of a plurality";
In column 11, line 56, at the end of the line, delete "the";
In column 11, line 57, after "domain" insert --data--;
In column 12, line 4, after "point" remove the comma and insert --and--;
In column 12, line 6, after "indicating" delete "the";
In column 12, line 6, after "of" change "said" to --a--;
In column 12, line 12, after "termination" delete "point";
In column 12, line 19, after "gas" delete "in said blood";
In column 12, line 20, after "said" insert --blood--, and after "gas" change "content in said blood" to --concentration--;

UNITED STATES PATENT AND TRADEMARK OFFICE
CERTIFICATE OF CORRECTION

PATENT NO : 5,800,361
DATED : September 1, 1998
INVENTOR(S) : Rayburn

It is certified that error appears in the above-identified patent and that said Letters Patent is hereby corrected as shown below:

In column 12, line 21, after "said" insert --blood--;
In column 12, line 22, delete "paint" and insert --point--;
In column 12, line 38, after "being" change "the" to --a--;
In column 12, line 44, after "termination of" change "said" to --a--;
In column 12, line 48, delete "point".

Signed and Sealed this

Sixteenth Day of November, 1999

Attest:

Attesting Officer

Q. TODD DICKINSON

Acting Commissioner of Patents and Trademarks